United States Patent
Davis et al.

(10) Patent No.: US 6,291,172 B1
(45) Date of Patent: Sep. 18, 2001

(54) DIAGNOSTIC ASSAY FOR DIABETES MELLITUS BASED ON MUTATIONAL BURDEN

(75) Inventors: Robert E. Davis; Corinna Herrnstadt, both of San Diego, CA (US)

(73) Assignee: Mitokor, San Diego, CA (US)

( * ) Notice: Subject to any disclaimer, the term of this patent is extended or adjusted under 35 U.S.C. 154(b) by 0 days.

(21) Appl. No.: 09/302,682

(22) Filed: Apr. 30, 1999

Related U.S. Application Data

(63) Continuation-in-part of application No. 09/272,904, filed on Mar. 19, 1999, which is a continuation-in-part of application No. 09/200,419, filed on Nov. 23, 1998, now Pat. No. 6,146,831, which is a division of application No. 08/734, 564, filed on Oct. 21, 1996, now Pat. No. 5,840,493, which is a continuation of application No. 08/397,808, filed on Mar. 3, 1995, now Pat. No. 5,888,498.

(51) Int. Cl.[7] .............................. C12P 19/34; C12Q 1/68; C07H 21/04; C07H 21/02
(52) U.S. Cl. ......................... 435/6; 435/91.1; 536/22.1; 536/23.1
(58) Field of Search .............................. 435/6; 536/22.1, 536/23.1

(56) References Cited

U.S. PATENT DOCUMENTS

| | | | |
|---|---|---|---|
| 5,840,493 | 11/1998 | Davis et al. | 435/6 |
| 5,888,498 | 3/1999 | Davis et al. | 424/93.21 |

FOREIGN PATENT DOCUMENTS

| | | |
|---|---|---|
| WO 91/19815 | 12/1991 | (WO) . |
| WO 95/26973 | 10/1995 | (WO) . |
| WO 98/17826 | 4/1998 | (WO) . |

OTHER PUBLICATIONS

Alcolado et al., *Diabetologia* 37:372–376, 1994.
Chemical Abstracts 124(5): Abstract No. 052875N.
Chemical Abstracts 128(25): Abstract No. 307167K.
Chemical Abstracts 130(3): Abstract No. 023761R.
Chemical Abstracts 130(19): Abstract No. 250712U.
Chemical Abstracts 131(25): Abstract No. 332941C.
Chemical Abstracts 132(14): Abstract No. 176567Y.
Derwent World Patent Index, Abstract No. C1995–358577.
Derwent World Patent Index, Abstract No. C1998–261517.
Dowton et al., *Clinical Chemistry A1*: 785–794, 1995.
Gerbitz et al., *Biochimica et Biophysica Acta 1271*:253–260, 1995.
Gerbitz et al., *Diabetes* 45:113–125, 1996.
Goto, *Muscle & Nerve*, Suppl 3: S107–S112, 1995.
Hames et al, editors *Nucleic Acid Hybridisation*. IRL Press. Washington D.C. (1985) pp. 17–18, & 30–45.
Hinokio et al., *Muscle& Nerve* Suppl. 3:S142–149, 1995.
Kadowaki et al., *Muscle& Nerve*, Suppl 3: S137–S141, 1995.
Kadowaki et al., *New England Journal of Medicine 330*:962–968. 1994.
Kishimoto et al., *Diabetologia* 38 :193–200, 1995.
"Letters to the Editor", *Diabetologia* 38:376–379, 1995.
Mathews et al., *Faseb J.* 9:1638–1642, 1995.
Oka et al., *Diabetes Res. Clin. Pract.* 24 Suppl., S117–S121, 1994.
Oka et al., *Muscle& Nerve*, Suppl 3: S131–S141, 1995.
Otabe et al., *J. Clin Endocrinol Metab.* 79(3):768–771, 1994.
Suzuki et al., *Diabetes Care* 17(11):1428–1432, 1994.
Anderson et al., "Sequence and Organization of the Human Mitochondrial Genome,"*Nature 290*:457–465, 1981.
Egawhary et al., "Diabetic Complications and the Mechansim of the Hyperglycaemia–Induced Damage to the mt DNA of Cultured Vascular Endothelial Cells: (I) Characterization of the 4977 Base Pair Deletion and 13 bp Flanking Repeats," *Biochemical Society Transactions* 23:518S, 1995.
Gerbitz et al., "Mitochondria and Diabetes. Genetic, Biochemical, and Clinical Implications of the Cellular Energy Circuit," *Diabetes* 45(2):113–125, 1996.
Johns, "Mitochondrial DNA and Disease," *The New England Journal of Medicine* 333(10):638–644, 1995.
King and Attardi, "Human Cells Lacking mtDNA: Repopulation with Exogenous Mitochondria by Complementation," *Science* 246:500–503, 1989.
Luft, "The Development of Mitochondrial Medicine," *Proceedings of the National Academy of Sciences* 91:8731–8738, 1994.
Mathews et al., "A Point Mutation in the Mitochondriral DNA of Diabetes–Prone BHE/cdb Rats," *FASEB Journal* 9:1638–1642, 1995.
Miller et al., "Creation and Characterization of Mitochondrial DNA–Depleted Cell Lines with 'Neuronal–Like' Properties," *J. Neurochem.* 67(5): 1897–1907, 1996.
Suzuki et al., "Diabetes With Mitochondrial Gene tRNA$^{LYS}$ Mutation," *Diabetes Care* 17(11):1428–1432, 1994.
Swerdlow et al., "Origin and Functional Consequences of the Complex I Defect in Parkinson's Disease," *Annals of Neurology* 40:663–671, 1996.

(List continued on next page.)

Primary Examiner—Carla J. Myers
Assistant Examiner—Arun Chakrabarti
(74) Attorney, Agent, or Firm—Seed Intellectual Property Law Group PLLC

(57) ABSTRACT

The present invention relates to genetic mutations in mitochondrial genes that segregate with diabetes mellitus. The invention provides methods for detecting such mutations, as a diagnostic for diabetes mellitus, either before or after the onset of clinical symptoms. Examples of specific mutations in the ATP synthase 8/6 sequence and tRNA$^{Lys}$ sequence are given. The invention also provides treatments for dysfunctions due to genes for mitochondrial functions that segregate with diabetes mellitus. Cybrid cell lines are described which are useful as model systems for the study of the mitochondrial metabolic disorders that are associated with diabetes mellitus, and for identifying therapeutic compounds and treatments for this disease.

5 Claims, 2 Drawing Sheets

OTHER PUBLICATIONS

Wallace, "Mitochondrial Genetics: A Paradigm for Aging and Degenerative Diseases,"*Science* 256:628–632, 1992.

Shoffner et al., Myoclonic epilepsy and ragged–red fiber disease (MERRF) is associated with a mitochondrial DNA tRNA lys mutation. Cell, vol. 61, pp. 931–937, Jun. 1990.*

Matthews et al., "Analytical strategies for the use of DNA probes", Analytical Biochemistry, vol. 169, pp. 1–25, 1988.*

Kameoka et al., "Impaired Insulin Secretion in Japanese Diabetic Subjects With an A–to–G Mutation at Nucleotide 8296 of the Mitochondiral DNA in tRNA$^{Lys}$," *Diabetes Care* 21(11): 2034–2035, Nov. 1998.

Kameoka et al., "Novel Mitochondiral DNA Mutation in tRNA$^{Lys}$(8296A→G) Associated with Diabetes,"*Biochemical And Biophysical Research Communications* 245(2): 523–527, 1998.

Lee et al., "Mitochondrial Gene Transfer Ribonucleic Acid (tRNA)$^{Leu(UUR)}$ 3243 and tRNA$^{Lys}$ 8344 Mutations and Diabetes Mellitus in Korea," *Journal of Clinical Endocrinology and Metabolism* 82(2): 372–374, 1997.

* cited by examiner

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 23 base pairs
       (B) TYPE: nucleic acid
       (C) STRANDEDNESS: double
       (D) TOPOLOGY: linear (xi) SEQUENCE DESCRIPTION: SEQ ID NO:1:

GCCCACTGTA AAGCTAAGTT AGC                                          23

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: double
       (D) TOPOLOGY: linear (xi) SEQUENCE DESCRIPTION: SEQ ID NO:2:

TAGTCGGTTG TTGATGAGAT AT                                           22

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: double
       (D) TOPOLOGY: linear (xi) SEQUENCE DESCRIPTION: SEQ ID NO:3:

CGTCTTGCAC TCATGAGCTG TCC                                          23

(2) INFORMATION FOR SEQ ID NO:4:

(i) SEQUENCE CHARACTERISTICS:
       (A) LENGTH: 25 base pairs
       (B) TYPE: nucleic acid
       (C) STRANDEDNESS: double
       (D) TOPOLOGY: linear (xi) SEQUENCE DESCRIPTION: SEQ ID NO:4:

ATTTTCGTTC ATTTTGGTTC TCAGG                                        25

(2) INFORMATION FOR SEQ ID NO:5:

(i) SEQUENCE CHARACTERISTICS:
       (A) LENGTH: 25 base pairs
       (B) TYPE: nucleic acid
       (C) STRANDEDNESS: double
       (D) TOPOLOGY: linear (xi) SEQUENCE DESCRIPTION: SEQ ID NO:5:

TAGCATTAAC CTTTTAAGTT AAAGA                                        25

(2) INFORMATION FOR SEQ ID NO:6:

(i) SEQUENCE CHARACTERISTICS:
       (A) LENGTH: 19 base pairs
       (B) TYPE: nucleic acid
       (C) STRANDEDNESS: double -continued

```
        (D) TOPOLOGY: linear (xi) SEQUENCE DESCRIPTION: SEQ ID NO:6:

TCGTTCATTT TGGTTCTCA                                                    19

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:7:

GTAAAACGAC GGCCAG                                                       16

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

CAGGAAACAG CTATGAC                                                      17
```

DIAGNOSTIC ASSAY FOR DIABETES MELLITUS BASED ON MUTATIONAL BURDEN

CROSS-REFERENCE TO RELATED APPLICATIONS

This application is a Continuation-In-Part of U.S. application Ser. No. 09/200,419 filed Nov. 23, 1998, now U.S. Pat. No. 6,146,831, which is a Divisional Application of U.S. application Ser. No. 08/734,564 filed Oct. 21, 1996 (issued on Nov. 24, 1998 as U.S. Pat. No. 5,840,493); this application is also a Continuation-In-Part of U.S. application Ser. No. 09/272,904 filed Mar. 19, 1999, which is a Continuation of U.S. application Ser. No. 08/397,808 filed Mar. 3, 1995 (issued on Mar. 30, 1999 as U.S. Pat. No. 5,888,498).

TECHNICAL FIELD

The present invention relates generally to model systems for diseases that involve defects in the function of mitochondria and specific mutational burdens. The invention also relates to the use of these model systems for screening drugs and evaluating the efficacy of treatments for those diseases. In particular, the invention relates to the diagnosis and treatment of late onset diabetes mellitus and related pathologies, such as impaired glucose tolerance and insulin dependent or non-insulin dependent diabetes.

BACKGROUND OF THE INVENTION

Diabetes mellitus is a common degenerative disease affecting 5 to 10 percent of the population in developed countries. It is a heterogeneous disorder with a strong genetic component; monozygotic twins are highly concordant and there is a high incidence of the disease among first degree relatives of affected individuals. The propensity for developing diabetes mellitus is reportedly maternally inherited, suggesting a mitochondrial genetic involvement. (Alcolado, J. C. and Alcolado, R., *Br. Med. J.* 302:1178–1180 (1991); Reny, S. L., *International J Epidem.* 23:886–890 (1994)).

Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient non-insulin dependent diabetes (NIDDM) each year. Some of these individuals further progress to insulin dependent diabetes mellitus (IDDM). This form of NIDDM or IDDM is associated with decreased release of insulin by pancreatic beta cells and/or a decreased end-organ response to insulin. Other symptoms of diabetes mellitus and conditions that precede or are associated with diabetes mellitus include: obesity, vascular pathologies, peripheral and sensory neuropathies, blindness, and deafness.

Due to the strong genetic component of diabetes mellitus, the nuclear genome has been the main focus of the search for causative genetic. mutations. However, despite intense effort, nuclear genes that segregate with diabetes mellitus are known only for rare mutations in the insulin gene, the insulin receptor gene, the adenosine deaminase gene and the glucokinase gene.

Clearly, a reliable diagnosis of late onset diabetes at its earliest stages is critical for efficient and effective intercession and treatment of this debilitating disease. There is a need for a non-invasive diagnostic assay that is reliable at or before the earliest manifestations of late onset diabetes symptoms. There is also a need for developing therapeutic regimens or drugs for treating both the symptoms of diabetes mellitus and of the disease itself.

The present invention satisfies these needs for a useful diagnostic and effective treatment of late onset diabetes and provides related advantages, as well.

SUMMARY OF THE INVENTION

The present invention relates to the identification of defects in mitochondrial function, which segregate with late onset diabetes. The invention provides methods for detecting such defects as a diagnostic for late onset diabetes, either before or after the onset of clinical symptoms. More specifically, the present invention provides a method for detecting the presence of or risk of developing diabetes mellitus in a subject comprising comparing (i) a mutational burden at one or more nucleotide positions in an ATP synthase gene in a sample from the subject with (ii) the mutational burden at one or more corresponding nucleotide positions in a control sample, and therefrom identifying the presence of or risk of developing diabetes mellitus. In certain embodiments the mutational burden relates to a mutation in an ATP synthase gene at nucleotide position 8371, 8374, 8383, 8386, 8392, 8395, 8396, 8398, 8401, 8404, 8410, 8419, 8422, 8423, 8428, 8450, 8459, 8463, 8467, 8470, 8473, 8474, 8485, 8486, 8487, 8488, 8491, 8503, 8506, 8508, 8509, 8512, 8539, 8541, 8557, 8562, 8566, 8568 or combinations thereof. In certain other embodiments, at least one mutation is a silent mutation, missense mutation, or combination thereof.

In other embodiments the invention provides a method for detecting the presence of or risk of developing diabetes mellitus in a subject, comprising comparing (i) a mutational burden at one or more nucleotide positions in a $tRNA^{Lys}$ gene in a sample from the subject with (ii) the mutational burden at one or more corresponding nucleotide positions in a control sample. and therefrom identifying the presence of or risk of developing diabetes mellitus. In certain embodiments the mutational burden relates to a mutation in a $tRNA^{Lys}$ gene at nucleotide position 8336, 8345, 8348, 8349, 8351 or combinations thereof. In certain further embodiments of any of the above embodiments of the invention, the presence of the mutation is detected by a technique that may be hybridization with oligonucleotide probes, a ligation reaction, a polymerase chain reaction or single nucleotide primer-guided extension assay, or variations thereof.

It is another aspect of the present invention to provide a method of detecting genetic mutations which cause diabetes mellitus or indicate a predisposition to develop diabetes mellitus, comprising determining the sequence of at least one mitochondrial ATP synthase gene from humans known to have diabetes mellitus; comparing the sequence to that of the corresponding wildtype mitochondrial ATP synthase gene; and identifying mutations in the humans which correlate with the presence of diabetes mellitus.

Turning to another aspect, the invention provides an isolated nucleotide sequence which is at least partially complementary to a mitochondrial DNA sequence, wherein the isolated sequence contains at least one mutation in an ATP synthase subunit 8/6 gene which correlates with the presence or risk of diabetes mellitus. In another aspect the invention provides an isolated nucleotide sequence which is at least partially complementary to a mitochondrial DNA sequence, wherein the isolated sequence contains at least one mutation in a tRNA$^{Lys}$ gene which correlates with the presence or risk of diabetes mellitus. In another aspect the invention provides an isolated nucleotide sequence which is at least partially complementary to a mitochondrial DNA sequence, wherein the isolated sequence contains at least one mutation located between mitochondrial DNA nucleotides 8295 and 8571 which correlates with the presence or risk of diabetes mellitus. In certain embodiments of the above aspects of the invention directed to an isolated nucleotide sequence, the isolated sequence is labeled with a detectable agent.

In yet another aspect, the invention provides a method of inhibiting the transcription or translation of one or more mutant ATP synthase encoding nucleic acids a correlated with late onset diabetes mellitus, or the transcription of one or more mutant tRNAL$^{Lys}$ encoding nucleic acids correlated with late onset diabetes mellitus, the method comprising contacting the ATP synthase or tRNA$^{Lys}$ encoding nucleic acids with antisense sequences specific to the mutant nucleic acids; and allowing hybridization between target mutant ATP synthase or tRNA$^{Lys}$ encoding nucleic acids and the antisense sequences. In certain embodiments, hybridization is performed under conditions wherein the antisense sequences bind to and inhibit transcription or translation of target mutant ATP synthase 8/6 encoding nucleic acid or inhibit transcription of target mutant tRNA$^{Lys}$ encoding nucleic acid without preventing transcription or translation of the corresponding wild-type nucleic acids or other mitochondrial genes. In certain embodiments, the mutant ATP synthase or tRNA$^{Lys}$ encoding nucleic acids are RNA.

The present invention also provides, in another aspect, a method for evaluating a compound for use in diagnosis or treatment of diabetes mellitus, the method comprising contacting a predetermined quantity of the compound with cultured cybrid cells having genomic DNA originating from a $\rho^0$ cell line and mitochondria originating from tissue of a human having a disorder that is associated with late onset diabetes mellitus; measuring a mitochondrial complex V activity that is affected by the mutant mitochondrial DNA in said cybrid cells; and correlating a change in the mitochondrial complex V activity with effectiveness of the compound. In on embodiment, the $\rho^0$ cell line is immortal.

Turning to another aspect, the invention provides a method for evaluating a compound for its utility in the diagnosis and treatment of diabetes mellitus, comprising inducing differentiation of cultured undifferentiated cybrid cells having genomic DNA originating from a $\rho^0$ cell line and mitochondria originating from tissue of a human having a disorder that is associated with late onset diabetes mellitus; contacting a predetermined quantity of the compound with these cybrid cells; measuring a mitochondrial complex V activity that is affected by mutant mitochondrial DNA in the cybrid cells and correlating a change in the mitochondrial complex V activity with effectiveness of the compound in the diagnosis or treatment of diabetes mellitus. In certain embodiments the $\rho^0$ cell line is immortal.

In another embodiment the invention provides a method for detecting the presence of diabetes mellitus in a human subject, comprising the steps of obtaining a biological sample containing mitochondria from the subject; and determining the presence of at least one polypeptide encoded by a mitochondrial ATP synthase gene. In certain embodiments the presence of the polypeptide is determined with at least one monoclonal antibody or polyclonal antibody.

It is another aspect of the present invention to provide a method for detecting the presence or risk of developing diabetes mellitus in a human, the method comprising determining the presence in a biological sample from a human of a nucleic acid sequence having a mutational burden at one or more nucleotide positions in a sequence region corresponding to a wildtype mitochondrial DNA sequence, wherein the mutational burden correlates with the presence of or risk of developing diabetes mellitus.

Another aspect of the invention provides an isolated nucleotide sequence which is at least partially complementary to a mitochondrial DNA sequence, the isolated sequence having a mutational burden at one or more nucleotide positions in a sequence region corresponding to a wildtype mitochondrial DNA sequence, wherein the mutational burden correlates with the presence of or risk of developing diabetes mellitus.

In still another aspect the invention provides a method for evaluating a compound for use in diagnosis or treatment of diabetes mellitus, comprising contacting a predetermined quantity of the compound with cultured cybrid cells having genomic DNA originating from a $\rho^0$ cell line and mitochondria originating from tissue of a human having a disorder that is associated with late onset diabetes mellitus; measuring a phenotypic trait in the cybrid cells that correlates with the presence of the mitochondria and that is not present in cultured cybrid cells having genomic DNA originating from a $\rho^0$ cell line and mitochondria originating from tissue of a human free of a disorder that is associated with late onset diabetes mellitus; and correlating a change in the phenotypic trait with effectiveness of the compound.

These and other aspects of the present invention will become evident upon reference to the following detailed description and attached drawings. In addition, various references are set forth herein which describe in more detail certain aspects of this invention, and are therefore incorporated by reference in their entireties.

DETAILED DESCRIPTION OF THE INVENTION

Figure 1:
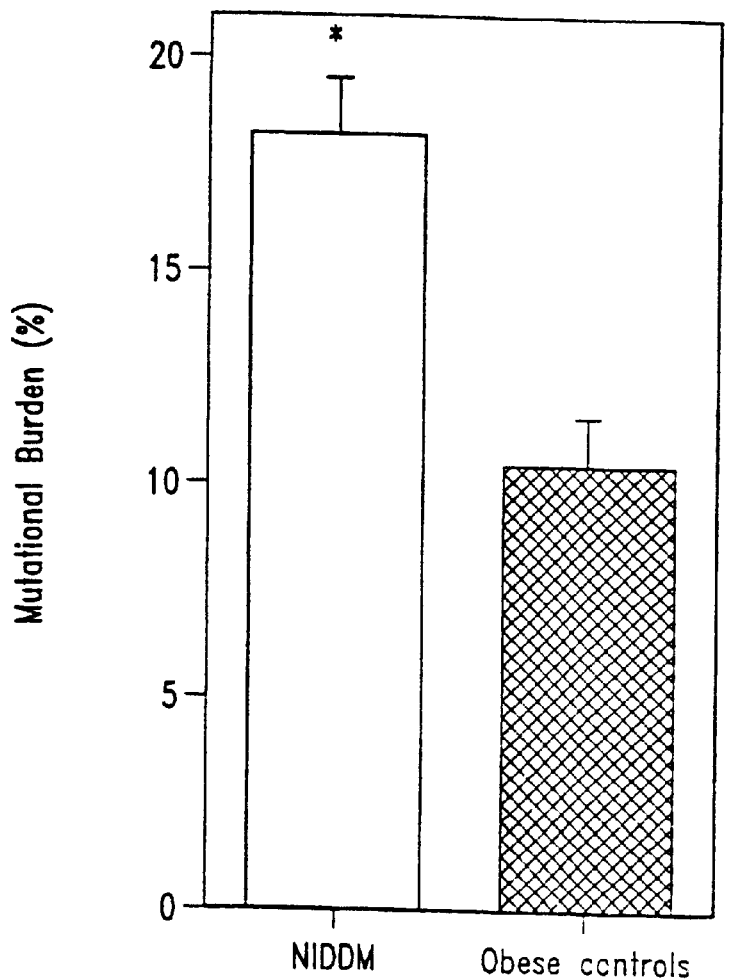
FIG. 1 depicts the increased mutational burden of the ATP synthase 8/6 genes in NIDDM.

The ability to ascertain which individuals are predisposed to develop IGT and diabetes mellitus is of enormous medical significance. The elucidation of the molecular events that underlie the progression from IGT to NIDDM is a quantum leap in the understanding of these conditions. A method for delaying, minimizing or preventing the onset of IGT or diabetes mellitus represents a major therapeutic advance.

The present invention represents an effective diagnostic assay of mitochondrial defects associated with late onset diabetes which is reliable at or before the earliest manifestations of late onset diabetes symptoms. Moreover, the invention also allows the suppression of the undesired biological activity associated with mutations and thus affords a therapeutic treatment for late onset diabetes.

Genetic defects in the genes that encode components of the electron transport chain are implicated in the switch from IGT to NIDDM. Perturbations of this. protein complex predictably lead to an alteration in the production of adenosine triphosphate (ATP), the main source of energy for cellular biochemical reactions.

When mitochondrial intracellular ATP levels drop, glucose transport into cells is impaired, metabolism of glucose is slowed and insulin secretion is decreased, all critical events in the switch from IGT to diabetes mellitus. Affected tissues are striated muscle (the major insulin-sensitive tissue) and pancreatic beta cells (insulin secreting cells). These target tissues contain non-dividing terminally differentiated cells that are susceptible to accumulation of mutations. Achieving a threshold level of mutations in mtDNA in pancreatic beta cells may precipitate a drop in insulin secretion, providing a molecular mechanism for the switch in disease phenotype from IGT to diabetes mellitus. In addition, a similar mechanism may precipitate a loss of insulin responsiveness in muscle.

Certain critical enzymes in the metabolism of glucose (hexokinases) and insulin secretion require ATP for proper function. Hexokinases and in particular glucokinase are bound to porin, a voltage dependent anion channel, located within the outer mitochondrial membrane. Porin, in turn, is apposed to the adenine nucleotide translocator of the inner mitochondrial membrane. Together these protein complexes form a conduit for delivery of ATP from the inner mitochondrial matrix to hexokinases bound to the outer membrane and for return of ADP generated by catalytic activity of these kinases. The ATP used by mitochondrial bound hexokinases is derived primarily from the mitochondrial matrix and not the cytoplasm. Hexokinases require mitochondrial ATP for activation.

ATP synthase is an important component of the electron transport chain, the cellular energy generating system located in the mitochondria of eukaryotic cells. ATP synthase, also known as complex V, is composed of at least eight subunits. At least six of these subunits are encoded by nuclear genes; the remaining two subunits (6 and 8) are encoded by mitochondrial genes. The two mitochondrial DNA encoded ATP synthase subunits are referred to herein collectively as ATP synthase 8/6, or individually as ATP synthase 8 and ATP synthase 6. Complex V activity, and the influence of defective ATP synthase 8/6 on complex V activity, can be measured by assays known to those skilled in the art. For example by way of illustration and not limitation, complex V-mediated enzymatic modification of suitable substrate molecules under reaction conditions known in the art can be measured spectrophotometrically.

Without wishing to be held to any particular theory, it has been postulated that the destructive effects of mutations in the ATP synthase genes arise from the production of oxygen radicals and other chemically unstable molecules due to collapse of the proton gradient across the intramitochondrial membrane. The effects of such free radicals are expected to be cumulative, especially in view of the lack of mechanisms for suppressing mutations in mitochondria.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

The terms used herein are not intended to be limiting of the invention. For example, the term "gene" includes cDNAs, RNA, or other polynucleotides that encode gene products. In using the terms "nucleic acid", "RNA", "DNA", etc., there is no intention to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives can be made and will hybridize to one another and to DNA and RNA, and the use of such analogues and derivatives is also within the scope of the present invention.

"Isolating" a substance refers to removing a material from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

"Expression" of a gene or nucleic acid encompasses not only cellular gene expression, but also the transcription and translation of nucleic acid(s) in cloning systems and in any other context. "At least one mutation" denotes the substitution, addition or deletion of at least one nucleotide anywhere in a nucleotide sequence. "Point mutations" are mutations within a nucleotide sequence that result in a change from one nucleotide to another; "silent mutations" are mutations that do not result in a change in the amino acid sequence encoded by the nucleotide sequence. "Mutational burden" refers to any qualitative assessment or quantification of the proportion of nucleic acid molecules in a sample having at least one mutation in a region of a specific nucleic acid sequence, relative to the proportion of nucleic acid molecules having the wildtype sequence for the corresponding nucleic acid region.

Portions of a mutated DNA sequence and a wildtype sequence are regarded as "corresponding" nucleic acid sequences, regions, fragments or the like, based on the convention of numbering wildtype DNA according to nucleotide position number, and then aligning the mutated sequence in a manner that maximizes the number of nucleotides that match at each position. For example, a mutated DNA sequence as provided herein may correspond to a wildtype sequence according to the convention for numbering wildtype mitochondrial DNA (mtDNA) nucleic acid positions disclosed in Anderson et al. (*Nature* 290:457, 1981), whereby a mutated DNA sequence is aligned with the mtDNA sequence of Anderson et al. such that at least 70%, preferably at least 80% and more preferably at least 90% of the nucleotides in a given sequence of at least 20 consecutive nucleotides of a sequence are identical. In certain preferred embodiments, a mutated DNA sequence is greater than 95% identical to a corresponding mtDNA sequence; In certain particularly preferred embodiments, a portion or region of a mutated DNA sequence is identical to a corresponding mtDNA sequence. Those oligonucleotide probes having sequences that are identical in corresponding regions of a mutated DNA sequence and mtDNA may be identified and selected following hybridization target DNA sequence analysis, to verify the absence of mutations in the target (e.g., mutant DNA-derived) sequence relative to the primer (e.g., wildtype mtDNA-derived) sequence.

In certain embodiments of the present invention, mutated DNA sequences may be found as extramitochondrial DNA (exmtDNA) and/or as pseudogene (i.e., highly homologous sequences that do not give rise to detectably transcribed RNA) DNA sequences. Such sequences are provided, for example, in co-pending U. S. application Ser. Nos. 09/098, 079 and 09/097,889, and in U.S. application Ser. No. 09/302, 681 which is being filed concurrently with the present application; these three applications are hereby incorporated by reference in their entireties.

Biological samples may comprise any tissue or cell preparation in which at least one nucleic acid sequence corresponding to a human mitochondrial DNA sequence, and in preferred embodiments corresponding to an ATP synthase gene sequence or a tRNA$^{Lys}$ sequence, can be detected, and may vary in nature accordingly, depending on the particular sequence(s) to be compared. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiable cell lines, transformed cell lines and the like. In certain preferred embodiments of the invention, the biological sample may be derived from a subject or biological source suspected of having or being at risk for having type 2 diabetes mellitus, and in certain preferred embodiments of the invention the subject or biological source may be known to be free of a risk or presence of such as disease.

The term "tissue" includes blood and/or cells isolated or suspended from solid body mass, as well as the solid body mass of the various organs. "Immortal" cell lines denotes cell lines that are so denoted by persons of ordinary skill, or are capable of being passaged preferably an indefinite number of times, but not less than ten times, without significant phenotypic alteration. "$\rho^0$ cells" are cells essentially depleted of functional mitochondria and/or mitochondrial DNA, by any method useful for this purpose.

The term "diabetes mellitus" is used in the claims to denote the disease that exhibits the symptoms of diabetes mellitus recognizable to one of ordinary skill in the art. "Diabetes mellitus" or "diabetes" may include, but need not be limited to, insulin-dependent diabetes mellitus (IDDM) and insulin-deficient non-insulin dependent diabetes mellitus (NIDDM) or type 2 diabetes mellitus (type 2 DM). For example, where it is desirable to determine whether or not a subject falls within clinical parameters indicative of type 2 DM, signs and symptoms of type 2 diabetes that are accepted by those skilled in the art may be used to so designate a subject, such as, e.g., clinical signs referred to in Gavin et al. (*Diabetes Care* 22(suppl. 1):S5–S19, 1999, American Diabetes Association Expert Committee on the Diagnosis and Classification of Diabetes Mellitus) and references cited therein, or other means known in the art for diagnosing diabetes mellitus. A phenotypic trait, symptom, mutation or condition "correlates" with diabetes mellitus if it is repeatedly observed in individuals diagnosed as having some form of diabetes mellitus, or if it is routinely used by persons of ordinary skill in the art as a diagnostic criterion in determining that an individual has diabetes mellitus or a related condition. Examples include: impaired insulin secretion, impaired response to insulin, or both.

Pre-clinical and/or asymptomatic conditions that correlate with the presence of mitochondrial mutations often observed in patients with diabetes mellitus, such as IGT, may represent steps in the progression in the disease. Individuals that lack the full panoply of such symptoms but carry mutations that "correlate" with diabetes mellitus are hereby defined as being "at risk" or having a "predisposition" for developing the fully symptomatic disease.

Although the invention focuses preferentially on humans afflicted with or at risk for developing diabetes mellitus as defined above, the invention also encompasses the analysis of tissues and preparations from relatives of persons having or being "at risk" for developing diabetes mellitus (which relatives may or may not themselves be at risk), and in vivo and in vitro. animal and tissue culture models that may exhibit one or more or all of the symptoms that correlate with the mitochondrial mutations of the invention.

Reference to particular buffers, media, reagents. cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The present invention provides cell lines whose genomic DNA is derived from cells that maintain a normal pancreatic β cell or insulin-responsive phenotype (such as, but not limited to, βTC6-F7, HIT, RINm5f, SH-SY5Y, TC-1 cells and INS-1 cells) and from mitochondria derived from an individual with a disorder known to be associated with a mitochondrial defect that segregates with late onset diabetes mellitus. The present invention also provides an immortal $\rho^0$ cell line that is undifferentiated, but is capable of being induced to differentiate, comprising cultured immortal cells having genomic DNA with origins in immortalized β cells or insulin-responsive cells (for example, TC6-F7, HIT-T15, RINm5f, TC-1, and INS-1 cells), and mitochondria derived from an individual with a disorder known to be associated with a mitochondrial defect that segregates with late onset diabetes mellitus.

Although the cells suggested for certain embodiments herein are immortalized pancreatic β cells, adipocytes, neuronal tissue and cells, myoblasts and insulin-responsive cells and platelets, the present invention is not limited to the use of such cells. Cells from different tissues (breast epithelium, colon, lymphocytes, etc.) or different species (human, mouse, etc.) are also useful in the present invention.

Throughout this application various publications are referenced within parentheses. The disclosures of these publications in their entireties are hereby incorporated by reference in this application.

Diagnostic Detection of Late Onset Diabetes-Associated Mutations Using Hybridization and Ligation Techniques In one aspect of the present invention, base changes in the ATP synthase or tRNA$^{Lys}$ sequences are detected and used as a diagnostic for late onset diabetes. A variety of techniques are available for isolating DNA and RNA from patient blood samples and for detecting mutations in isolated ATM synthase and tRNA$^{Lys}$ sequences. For example, the DNA from a blood sample is obtained by cell lysis following alkali treatment. Often, there are multiple copies of RNA message per DNA. Accordingly, it is useful from the standpoint of detection sensitivity to have a sample preparation protocol which isolates both forms of nucleic acid. Total nucleic acid may be isolated by guanidinium isothiocyanate/phenol-chloroform extraction, or by proteinase K/phenol-chloroform treatment. Commercially available sample preparation methods such as those from Qiagen Inc. (Chatsworth, Calif.) are also utilized.

As discussed more fully below, hybridization with one or more labeled probes containing the variant sequences under stringency conditions that result in specific binding to sequences complementary to these probes enables detection of late onset diabetes mutations. A quantitative or semi-quantitative measure (depending on the detection method) of mutational burden is obtained by comparing the amount of signal from, for example, a late onset diabetes probe to the amount from a wild-type (normal) probe.

Certain techniques, discussed more fully hereinbelow, are available for detecting specific mutations in the mitochondrial ATP synthase and tRNA$^{Lys}$ sequences. The detection methods include, for example, cloning and sequencing, ligation of oligonucleotides, use of the polymerase chain reaction and variations thereof (e.g., a PCR that uses 7-deaza-GTP), use of single nucleotide primer-guided extension assays, hybridization techniques using target-specific oligonucleotides that can be shown to preferentially bind to complementary sequences under given stringency conditions, and sandwich hybridization methods.

Cloning and sequencing of the ATP synthase and/or tRNA$^{Lys}$ sequences serves to detect late onset diabetes mutations in patients. Sequencing may be carried out with commercially available automated sequencers utilizing labeled primers or terminators. An alternate sequencing strategy is sequencing by hybridization using high density oligonucleotide arrays on silicon chips (Fodor et al., Nature 364:555–556 (1993); Pease et al., Proc. Natl. Acad Sci. USA 91:5022–5026 (1994)). Labeled target nucleic acid generated, for example, from PCR amplification of the target genes using fluorescently labeled primers, is hybridized with a chip containing a set of short oligonucleotides which probe regions of complementarity with the target sequence. The resulting hybridization patterns are used to reassemble the original target DNA sequence.

Mutational analysis is also carried out by ligation reaction methods based on ligation of oligonucleotide sequences which anneal immediately adjacent to each other on a target DNA or RNA molecule, including but not limited to the Ligase Chain Reaction or any other methods for the detection of specific mutations in nucleic acid sequences that are known to those skilled in the art (Wu and Wallace, Genomics 4:560–569 (1989); Landren et al., Science 241:1077–1080 (1988); Nickerson et al., Proc. Natl. Acad. Sci. 87:8923–8927 (1990); Barany, F., Proc. Natl. Acad. Sci. 88:189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., PCR Methods and Applications 1:5–16 (1991)).

Analysis of point mutations in DNA may also be carried out using polymerase chain reaction (PCR) and variations thereof (e.g., using 7-deaza GTP with or instead of dGTP). Mismatches are detected by competitive oligonucleotide priming under hybridization conditions where binding of the perfectly matched primer is favored (Gibbs et al., NucL Acids Res. 17:2437–2448 (1989)). In the amplification refractory mutation system technique (ARMS), primers are designed to have perfect matches or mismatches with target sequences either internal or at the 3' residue (Newton et al., NucL Acids Res. 17:2503–2516 (1989)). Under appropriate conditions, only the perfectly annealed oligonucleotide functions as a primer for the PCR reaction, thus providing a method of discrimination between normal and mutant (late onset diabetes) sequences.

Genotyping analysis of the ATP synthase and tRNA$^{Lys}$ sequences may also be carried out using single nucleotide primer-guided extension assays, where the specific incorporation of the correct base is provided by the high fidelity of the DNA polymerase (Syvanen et al., Genomics 8:684–692 (1990); Kuppuswamy et al., Proc. Natl. Acad. Sci. USA 88:1143–1147 (1991)). Another primer extension assay which allows for the quantification of mutational burden by simultaneously determining both wild-type and mutant nucleotides, is disclosed in U.S. application Ser. No. 08/410, 658 and U.S. application Ser. No. 081810,599, the disclosures of which are incorporated by reference. Means for quantitatively evaluating the results of primer extension assays are provided, for example, in U.S. application Ser. No. 09/289,793, which is hereby incorporated by reference as if set forth in its entirety.

Detection of single base mutations in target nucleic acids is conveniently accomplished by differential hybridization techniques using target-specific oligonucleotides (Suggs et al., Proc. Natl. Acad. Sci. 78:6613–6617 (1981); Conner et al., Proc. Natl. Acad. Sci. 80:278–282 (1983); Saiki et al., Proc. Natl. Acad Sci. 86:6230–6234 (1989)). Mutations are diagnosed on the basis of the higher thermal stability of the perfectly matched probes as compared to the mismatched probes. The hybridization reactions are carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection of the ATP synthase and/or tRNA$^{Lys}$ nucleic acid sequences by sandwich hybridization methods. In this strategy, the mutant and wildtype (nominal) target nucleic acids are separated from non-homologous DNA/RNA using a common capture oligonucleotide immobilized on a solid support and detected by specific oligonucleotide probes tagged with reporter labels. The captured oligonucleotides are immobilized on microtiter plate wells or on beads (Gingeras et al., J. Infect. Dis. 164:1066–1074 (1991); Richman et al., Proc. Natl. Acad. Sci. 88:11241–11245 (1991)).

While radio-isotopic labeled detection oligonucleotide probes are highly sensitive, non-isotopic labels are preferred due to concerns about handling and disposal of radioactivity. A number of strategies are available for detecting target nucleic acids by non-isotopic means (Matthews et al., Anal. Biochem. 169:1–25 (1988)). The non-isotopic detection method may be either direct or indirect.

In an indirect detection process, the oligonucleotide probe is generally covalently labeled with a hapten or ligand such as digoxigenin (DIG) or biotin. Following the hybridization step, the target-probe duplex may be detected by an antibody- or streptavidin-enzyme complex. Enzymes commonly used in DNA diagnostics are horseradish peroxidase and alkaline phosphatase. One particular indirect method, the Genius detection system (Boehringer Mannheim) may be especially useful for mutational analysis of mitochondrial genes. This indirect method uses digoxigenin as the tag for the oligonucleotide probe and is detected by an anti-digoxigenin-antibody-alkaline phosphatase conjugate.

Direct detection methods include the use of fluorophore-labeled oligonucleotides, lanthanide chelate-labeled oligonucleotides or oligonucleotide-enzyme conjugates. Examples of fluorophore labels are fluorescein, rhodamine and phthalocyanine dyes. Examples of lanthanide chelates include complexes of $Eu^{3+}$ and $Tb^{3+}$. Directly labeled oligonucleotide-enzyme conjugates are preferred for detecting point mutations when using target-specific oligonucleotides, as they provide very high sensitivities of detection.

Oligonucleotide-enzyme conjugates are prepared by a number of methods (Jablonski et al., *Nucl Acids Res.* 14:6115–6128 (1986); Li et al., *Nucl. Acids Res.* 15:5275–5287 (1987); Ghosh et al., *Bioconjugate Chem.* 1:71–76 (1990)), with alkaline phosphatase being the enzyme of choice for obtaining high sensitivities of detection. The detection of target nucleic acids using these conjugates may be carried out by filter hybridization methods or by bead-based sandwich hybridization (Ishii et al., *Bioconjugate Chemistry* 4:34–41 (1993).

Detection of the probe label may be accomplished using the following approaches. For radioisotopes, detection may be by autoradiography, scintillation counting or phosphor imaging. For hapten or biotin labels, probe may be detected by antibody or streptavidin bound to a reporter enzyme such as horseradish peroxidase or alkaline phosphatase, which is then detected by enzymatic means. For fluorophore or lanthanide-chelate labels, fluorescent signals may be measured with spectrofluorimeters with or without time-resolved mode or using automated microtiter plate readers. With enzyme labels, detection may be by color or dye deposition (p-nitrophenyl phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit Mich. or AMPPD and CSPD from Tropix, Inc.). Chemiluminescent detection may be carried out with X-ray or Polaroid film or by using single photon counting luminometers. This is the preferred detection format for alkaline phosphatase labeled probes.

The detection oligonucleotide probes range in size between 10–100 bases, and are preferably between 15 to 30 bases in length. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

The present invention also provides compositions and methods that are useful in pharmacogenomics, for the classification and/or stratification of a subject or a patient population. Such stratification may involve, for example, correlation of one or more single nucleotide position mutational burdens as provided herein with, for instance, one or more particular traits in a subject, and further, optionally, with clinical indicators of diabetes as described herein that provide evidence of the subject's responsiveness to, or the relative efficacy of, a particular therapeutic treatment.

As described herein, determination of a mutational burden at one or more specific nucleotide position in a nucleic acid sequence may be used to stratify a diabetic or pre-diabetic patient population. Accordingly, in another preferred embodiment of the invention, determination of such mutational burden in a biological sample from a subject may provide a useful correlative indicator for that subject. A subject so classified on the basis of one or more specific mutations may then be monitored using diabetes mellitus clinical parameters referred to above (e.g., Gavin et al, 1999 *Diabetes Care* 22 (suppl. 1):S5–S19), such that correlation between particular mtDNA mutations and any particular clinical score used to evaluate diabetes may be monitored. For example, stratification of a diabetic patient population according to mutational burden, such as at least one of the single nucleotide polymorphisms or point mutations provided herein, may provide a useful marker with which to correlate the efficacy of any candidate therapeutic agent being used in diabetic subjects. These and related advantages will be appreciated by those familiar with the art.

Diagnostic Detection of Diabetes Associated Mutations Using Antibodies

As an alternative to detection of mutations in the nucleic acids associated with the mutant sequences described herein, the protein products of these sequences may be analyzed using immune techniques. In particular, altered proteins (variant polypeptides) encoded by nucleic acids having point mutations in ATP synthase subunit 8 may be isolated and used to prepare antisera and monoclonal antibodies that specifically detect the products of the mutated genes, and not those of non-mutated or wild-type genes. Mutated gene products may also be used to immunize animals for the production of polyclonal antibodies. Recombinantly produced peptides can also be used to generate polyclonal antibodies. These peptides represent small fragments of gene products produced by expressing nucleic acid sequences to regions containing point mutations.

Antibodies provided by the invention may be polyclonal antibodies or monoclonal antibodies. Antibodies may also be fragments of monoclonal or polyclonal antibodies that retain antibody binding activities. "Antibodies" further includes recombinant or genetically engineered antibodies, or fragments thereof or fusion proteins having antibody activity, including single-chain antibodies.

As discussed, for example, in PCT/US93/10072, variant polypeptides encoded by nucleic acids with point mutations in ATP synthase subunit 8 are used to immunize an animal for the production of polyclonal antiserum. For example, a recombinantly produced fragment of a variant polypeptide is injected into a mouse along with an adjuvant so as to generate an immune response. Murine immunoglobulins which bind the recombinant fragment with a binding affinity of at least $1\times10^7$ $M^{-1}$ are harvested from the immunized mouse as an antiserum, and are optionally further purified by affinity chromatography or other means. Additionally, spleen cells are harvested from the mouse and fused to myeloma cells to produce a bank of antibody-secreting hybridoma cells. The bank of hybridomas is screened for clones that secrete immunoglobulins which bind the recombinantly produced fragment with an affinity of at least $1\times10^6$ $M^{-1}$. More specifically, immunoglobulins that selectively bind to the variant polypeptides but poorly or not at all to wild-type polypeptides are selected. either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic oligonucleotides, etc.) as well as by a variety of different techniques.

The DNA sequences are expressed in hosts after the sequences have been operably linked to (i.e., positioned to ensure the functioning of) an expression control sequence.

These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362, incorporated herein by reference thereto.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryofic expression hosts, and, optionally, sequences necessary for replication of a vector.

E. coli is one prokaryotic host useful particularly for cloning DNA sequences of the present invention. Other microbial hosts suitable for use include bacilli, such as Bacillus subtilus, and other enterbacteriaceae, such as Salmonella, Serratia, and various Pseudomonas species. Expression vectors made in these prokaryotic hosts will typically contain expression control sequences compatible with the host cell (e.g., an origin of replication). In addition, any number of a variety of well-known promoters may be used, such as the lactose promoter system, a tryptophan Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, may also be used for expression. Saccharomyces is a suitable host with suitable vectors having expression control sequences, such as promoters, including 3-phosphoglycerate kinase or other glycolytic enzymes, and an origin of replication, termination sequences, etc., as desired.

In addition to microorganisms, mammalian tissue cell culture may be used to express and produce the polypeptides of the present invention. Eukaryotic cells are preferred, because a number of suitable host cell lines capable of secreting intact human proteins have been developed in the art, including CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences include promoters derived from immunoglobulin genes, SV40, Adenovirus, Bovine Papilloma Virus, and so forth. The vectors containing the DNA segments of interest (e.g., sequences encoding a variant polypeptide) are transferred into the host cell by well-known methods, which vary depending on the type of cellular host. For example, calcium chloride transfection is commonly utilized for-prokaryotic cells, whereas calcium phosphate treatment or electroporation is useful for other cellular hosts.

Test Kits

The methods described herein readily lend themselves to the formulation of test kits for use in diagnosis. Such a kit comprises a carrier compartmentalized to receive in close confinement one or more containers, wherein a first container contains suitably labeled DNA or immunological probes. Other containers generally contain reagents useful in the localization of the labeled probes, such as enzyme substrates. Still other containers contain restriction enzymes, buffers, etc., together with instructions for use.

Antisense Embodiments

Protein synthesis may be inhibited through the use of antisense or triplex oligonucleotides, analogues or expression constructs. These methods entail introducing into a cell a nucleic acid sufficiently complementary in sequence so as to specifically hybridize to a target nucleic acid. Antisense methodology inhibits the normal processing, translation or half-life of the target nucleic acid. A variety of antisense methods are well known to one skilled in the art. (Hélenè et al., *Biochem. BioPhys. Acta* 1049:99–125 (1990).) Procedures for inhibiting gene expression in cell culture and in vivo are described, for example, by C. F. Bennett et al. (*J Liposome Res.* 3:85 (1993) and C. Wahlestedt et al., *Nature* 363:260 (1993)).

Suppressing the effects of the mutations through antisense technology provides an effective therapy for diabetes mellitus. Antisense agents target mitochondrial DNA, by triplex formation with double-stranded DNA, by duplex formation with single stranded DNA during transcription, or both. Antisense agents also target messenger RNA coding for mutated ATP synthase gene(s). Since the sequences of both the DNA and the rnRNA are essentially the same, it is not necessary to determine accurately the precise target to account for the desired effect.

As used herein, an "antisense" oligonucleotide is one that base pairs with single stranded DNA or RNA by Watson-Crick base pairing and with duplex target DNA via Hoogsteen hydrogen bonds. Antisense and triplex methods generally involve the treatment of cells or tissues with a relatively short oligonucleotide, although longer sequences may be used to achieve inhibition. The oligonucleotide is either deoxyribo- or ribonucleic acid or analogues thereof, and must be of sufficient length to form a stable duplex or triplex with the target RNA or DNA at physiological temperatures and salt concentrations. It should also be of sufficient complementarity or sequence specificity to specifically hybridize to the target nucleic acid. Oligonucleotide lengths sufficient to achieve this specificity are generally about 10 to 60 nucleotides long, preferably about 10 to 20 nucleotides long. However, hybridization specificity is not only influenced by length and physiological conditions but may also be influenced by such factors as GC content and the primary sequence of the oligonucleotide. Such principles are well known in the art.

The composition of the antisense or triplex oligonucleotides influences the efficiency of inhibition. For example, it is preferable to use oligonucleotides that are resistant to degradation by the action of endogenous nucleases. Nuclease resistance will confer a longer in vivo half-life to the oligonucleotide, thus increasing its efficacy and reducing the required dose.

Antisense therapy is extremely efficient since only a few copies per cell are required to achieve complete inhibition. Greater efficacy is obtained by modifying the oligonucleotide so that it is more permeable to cell membranes. Such modifications are well known in the art and include the alteration of the negatively charged phosphate backbone bases, or modification of the sequences at the 5' or 3' terminus with agents such as intercalators and cross-linking molecules. Specific examples of such modifications include oligonucleotide analogs that contain methylphosphonate (Miller, P.S., *Biotechnology* 2:358–362 (1991)), phosphorothioate (Stein, *Science* 261:1004–1011 (1993)) and phosphorodithioate linkages (Brill, W. K-D., *J. Am. Chem. Soc.* 111:2322 (1989)). Other types of linkages and modifications exist as well, such as a polyamide backbone in peptide nucleic acids (Nielson et al., *Science* 254:1497 (1991)), formacetal (Matteucci, M., *Tetrahedron Lett.* 31:2385–2388 (1990)) carbamate and morpholine linkages as well as others known to those skilled in the art.

Vectors containing antisense nucleic acids may be employed to express antisense message to reduce the expression of the target nucleic acid, and therefore its activity. Such vectors are known or can be constructed by those skilled in the art and should contain all expression elements necessary to achieve the desired transcription of the antisense or triplex sequences. Other beneficial characteristics may also be contained within the vectors, such as mechanisms for recovery of the nucleic acids in a different form.

Phagemids are a specific example of such beneficial vectors because they are used either as plasmids or as bacteriophage vectors. Examples of other vectors include viruses, such as bacteriophages, baculoviruses and retroviruses, cosmids, plasmids, liposomes and other recombination vectors. The vectors may also contain elements for use in either procaryotic or eukaryotic host systems. One of ordinary skill in the art will know which host systems are compatible with a particular vector.

The vectors may be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by references, and in Ausubel et al., *Current Protocols in Molecular Biology*, John Wiley and Sons, Baltimore, Md. (1989), which is also hereby incorporated by reference. The methods include, for example, stable or transient transfection, lipofection, electroporation and infection with recombinant viral vectors.

Introduction of nucleic acids by infection offers several advantages. Higher efficiency is achieved due to their infectious nature. Moreover, viruses are very specialized and typically infect and propagate in specific cell types. Thus, their natural specificity is used to target the antisense vectors to specific cell types in vivo or within a tissue or mixed culture of cells. Viral vectors may also be modified with specific receptors or ligands to alter target specificity through receptor mediated events.

A specific example of a viral vector for introducing and expressing antisense nucleic acids is the adenovirus derived vector Adenop53TX. This vector expresses a herpes virus thymidine kinase (TX) gene for either positive or negative selection and an expression cassette for desired recombinant sequences such as antisense sequences. This vector may be used to infect cells including most cancers of epithelial origin, glial cells and other cell types. This vector, as well as others that exhibit similar desired fuictions, may be used to treat a mixed population of cells to selectively express the antisense sequence of interest. A mixed population of cells can include, for example, in vitro or ex vivo culture of cells, a tissue or a human subject.

Additional features can be added to the vector to ensure its safety and/or enhance its therapeutic efficacy. Such features include, for example, markers that are used to negatively select against cells infected with the recombinant virus. An example of such a negative selection marker is the TK gene, which confers sensitivity to the antibiotic gancyclovir. Negative selection is therefore a means by which infection is controlled because it provides inducible suicide through the addition of antibiotics. Such protection ensures that if, for example, mutations arise that produce mutant forms of the viral vector or antisense sequence, cellular transformation will not occur. Moreover, features that limit expression to particular cell types can also be included. Such features include, for example, promoter and expression elements that are specific for the desired cell type.

In addition to the specificity afforded by the antisense agents, the target RNA or genes may be irreversibly modified by incorporating reactive functional groups in these molecules which covalently link the target sequences, e.g., by alkylation.

In a preferred embodiment, antisense agents target messenger RNA coding for the mutated ATP synthase or tRNA$^{Lys}$. Since the sequences of both the DNA and the mRNA are the same, it is not necessary to determine accurately the precise target to account for the desired effect.

To demonstrate the ability to affect expression of mitochondrial ATP synthase or tRNA$^{Lys}$ genes, an oligonucleotide designed to hybridize near the 5'-end of the wild type ATP synthase or tRNA$^{Lys}$ gene or gene transcript is synthesized. When the antisense oligonucleotide is present in a suitable cell culture, the cells will die if the electron transport chain is interrupted. Control fibroblasts treated with complementary ('sense') oligonucleotide, or left untreated, will exhibit no such effects.

Since the diagnostic test of the present invention may be used to determine which of the specific late onset diabetes mutations exists in a particular late onset diabetes patients, one can "customize" treatment of the patient with antisense oligonucleotides directed only to the detected mutations. When combined with the present diagnostic test, this approach to "patient-specific therapy" results in treatment restricted to the specific mutations detected in a patient.

Antisense oligonucleotide therapeutic agents with a high degree of pharmaceutical specificity allow for the combination of two or more antisense therapeutics at the same time, without increased cytotoxic effects. Thus, when a patient is diagnosed as having two or more late onset diabetes mutations in ATP synthase or tRNA$^{Lys}$ sequences, the therapy may be tailored to treat the multiple mutations simultaneously. This patient-specific therapy circumvents the need for 'broad spectrum' antisense treatment using all possible mutations and minimizes the exposure of the patient to any unnecessary antisense therapeutic treatment. The end result is less costly treatment, with less chance for toxic side effects.

Selective intervention directed to impairing mutations related to mitochondrial defects may also be achieved by using ribozymes. Ribozymes are a class of RNA molecules that catalyze strand scission of RNA molecules independent of cellular proteins. Specifically, ribozymes may be directed to hybridize and cleave target mitochondiial mRNA molecules. The cleaved target RNA cannot be translated, thereby preventing synthesis of essential proteins which are critical for mitochondrial function. The therapeutic application thus involves designing a ribozyme which incorporates the catalytic center nucleotides necessary for finction and targeting it to mRNA molecules which encode for dysfunctional ATP synthase subunits or tRNA$^{lys}$. The ribozymes may be chemically synthesized and delivered to cells or they can be expressed from an expression vector following either permanent or transient transfection. Therapy is thus provided by the selective removal of mutant mRNAs in defective mitochondria.

Cybrids

Methods for depleting mitochondrial DNA ("mtDNA") from cells and then transforming those cells with mitochondria from other cells to produce cytoplasmic hybrid or "cybrid" cell lines are known in the art. (e.g., King, M. P. and Attardi, B., *Science* 246:500–503 (1989).) The value of the reported cell lines is limited because the pathogenesis of a given disease may depend on cell type. Also, the techniques for mitochondrial transformation of human cells allow only limited short term studies. Care has to be taken in growing cultures since transformed, undifferentiated cells containing normally finctioning mitochondria are healthier than those containing defective mitochondria and therefore have a propagative advantage in culture. Over the course of several generations, cells with normally finctioning mitochondria would dominate the cellular population (ie., mutant mtDNA would be selected against) and cells containing defective mitochondria would be lost.

The different embodiments of the present invention overcome these limitations. First, using $\rho^0$ cells derived from cultures of cell lines in which different cellular manifestations of diabetes mellitus are observed permits analysis of changes in mitochondrial function and closely mimics the functional effects of mitochondrial dysfunction in pancreatic β cells and insulin-responsive cells (e.g., muscle, neurons, adipocytes, etc.). Secondly, by introducing mitochondria from diseased cells into an undifferentiated, immortal cell line, it is possible to maintain the transformants in culture almost indefinitely. Although it would be possible to study and use the undifferentiated cells themselves, it is preferred to take a sample of such cells, and then induce them to differentiate into the cell type that they are destined to become Mitochondria to be transferred to construct model systems in accordance with the present invention may be isolated from virtually any tissue or cell source. Cell cultures of all types-could potentially be used, as could cells from any tissue. However, cells that are implicated in insulin secretion or that are responsive to insulin, especially isolated pancreatic β0 cells, fibroblasts. brain tissue, myoblasts, and cell lines derived therefrom are preferred sources of donor mitochondria. Platelets are the most preferred, in part because of their ready abundance, and their lack of nuclear DNA. This preference is not meant to constitute a limitation on the range of cell types that are used as donor sources.

Recipient cells useful to construct models in accordance with the present invention are potentially cells of any type that may be maintained in culture, but immortalized cell lines are preferred because of their growth characteristics. Many such cell lines are commercially available, and new ones are isolated and rendered immortal by methods that are well known in the art. Although cultured cell lines are preferred, it is also possible that cells from another individual, e.g., an unaffected close blood relative, are useful; this could have certain advantages in ruling out non-mitochondrial effects. In any event, it is preferable to use recipient cells that can be induced to differentiate by the addition of particular chemical (e.g., hormones, growth factors, etc.) or physical (e.g., temperature, exposure to radiation such as U.V. radiation, etc.) induction signals.

It is most preferred that the recipient cells be selected such that they are of (or capable of being induced to become) the type that is most phenotypically affected in diseased individuals. For example, for constructing models for mitochondrial defects associated with diabetes, immortalized pancreatic β cell lines are most preferred.

However, the present invention also contemplates that the recipient cell line is a member of the group of cell lines consisting of a mammalian zygote, an embryonic cell capable of differentiating and giving rise to a tissue, an individual, or a germ cell line.

In some embodiments of the present invention mitochondria are transplanted into an immortal, differentiatable cell, line, and the transplanted cells are also immortal. The invention further teaches the induction of differentiation among a subpopulation of the immortal culture, which allows for the same experiments to be done as would otherwise have been possible had the transplant been made directly into the differentiated cells. For example, mitochondria from an NIDDM or diabetes mellitus patient are transplanted into an immortalized pancreatic β cell or adipocyte or myoblast or a cell line derived therefrom, subcultures of which are induced to differentiate into pancreatic β cells or fat or muscle cells. The phenotypic expression of the mitochondrial defects in this model system is thus observed in the very cell type that is most affected by the disease.

The only requirement for the method of isolating mitochondria is that the mitochondria be substantially purified from the source cells and that the source cells be sufficiently disrupted that there is little likelihood that the source cells will grow and proliferate in the culture vessels to which the mitochondria are added for transformation. Mitochondrial DNA (mtDNA) of the target cells may be removed, for example, by treatment with ethidium bromide. Presumably, this works by interfering with transcription or replication of the mitochondrial genome, and/or by interfering with mRNA translation. The mitochondria are thus rendered unable to replicate and/or produce proteins required for electron transport, and the mitochondria shut down, apparently permanently. However, it is important to note that it is not necessary for the purposes of this invention to use any particular method to remove the mitochondria or mitochondrial DNA.

The cybrid cells of this invention are useful for evaluating chemical compounds for potential utility in the diagnosis or treatment of diabetes mellitus, which encompasses: reducing or delaying the risk of developing diabetes mellitus, and/or treatment of a symptom of diabetes mellitus or a condition that is associated with late onset diabetes mellitus, and/or establishing whether and to what extent a test compound is capable of causing a specified trait to become more similar to those of control cells having mitochondria that lack said defect. This is accomplished by a) contacting a predetermined quantity of a test compound with cultured cybrid cells having genomic DNA originating from a $\rho^0$ cell line and mitochondriaoriginating from tissue of a human having at least one mutation in an ATP synthase gene or a tRNA$^{Lys}$ gene that is associated with late onset diabetes mellitus; and b) measuring a phenotypic trait in the cybrid cells that is affected by the mitochondrial defect; and c) establishing whether and to what extent the test compound is capable of causing the phenotypic trait to become more similar to that seen in control cells having mitochondria that lack the defect, which capability indicates that the compound has utility in the treatment of the disorder. Embodiments of the invention involving measurement of phenotype traits include but need not be limited to assays of mitochondrial complex V activity, which may further include assays of ATP synthase enzymatic activity and ATP production, assays of reactive oxygen species production, and other assays of electron transport chain activity known to those skilled in the art.

After appropriate clinical tests to determine a safe dosage using methods known in the medical and pharmaceutical arts, the test compounds having utility may be administered to humans suffering from or at risk for developing diabetes mellitus. Administration may take place by methods known in the art, e.g., orally, transdermally, by intradermal, intramuscular, subcutaneous, or intravenous injection, etc. Treatment with said compounds may prevent or delay the onset of diabetes mellitus, or will serve to treat at least one symptom of the disease.

Although the present invention is directed primarily towards model systems for diseases in which the mitochondria have metabolic defects, it is not so limited. Conceivably there are disorders wherein there are structural or morphological defects or anomalies, and the model systems of the present invention are of value, for example, to find drugs that address that particular aspect of the disease. In addition, there are certain individuals that have or are suspected of having extraordinarily effective or efficient mitochondrial function, and the model systems of the present invention are of value in studying such mitochondria. In addition, it may be desirable to put known normal mitochondria into cell lines having disease characteristics, in order to rule out the possibility that mitochondrial defects contribute to pathogenesis. All of these and similar uses are within the scope of the present invention. and the use of the phrase "mitochondrial defect" herein should not be construed to exclude such embodiments.

The following examples are offered by way of illustration and not limitation.

EXAMPLES

Example 1

DNA EXTRACTION FROM BLOOD SAMPLES

Blood samples (6–7 ml) from 9 NIDDM patients and 6 non-NIDDM (5 controls and 1 Alzheimer's Disease patient) individuals were collected in EDTA Vacutainer tubes. 6 ml of blood was transferred to a centrifuge tube and 18 ml of dextran solution (3% dextran, average MW=250,000 kiloDaltons, 0.9% sodium chloride, 1 mM ethylenedinitrilo tetraacetate) was added and mixed. The tube was maintained at room temperature for 40 minutes without agitation to allow erythrocytes to sediment.

The plasma and leukocyte fraction was transferred to a 15 ml centrifuge tube and leukocytes were collected by centrifugation at 14,000 g for 10 minutes. The leukocyte pellet was resuspended in 3.6 ml of water and vortexed for 10 seconds to lyse remaining erythrocytes. 1.2 ml. of 0.6 M sodium chloride was added and the sample was again centrifuged at 14,000 g for 10 minutes to collect the leukocytes. The leukocyte pellet was resuspended in 0.4 ml of a solution containing 0.9% sodium chloride/1 mM EDTA, and stored at −80° C.

Total cellular DNA was isolated from 0.2 ml of the frozen leukocyte sample. The frozen leukocytes were thawed, then collected by centrifugation at 12,000 g in a microcentrifuge for 5 minutes. The cell pellet was washed once with 0.3 ml of Dulbecco's Phosphate Buffered Saline (PBS: Gibco BRL Life Technologies) and resuspended in 0.2 ml water. The leukocytes were lysed by incubating the sample for 10 minutes at 100° C. in a water bath. After the samples were brought to room temperature, cellular debris was pelleted by centrifugation at 14,000 g for 2 minutes. The supernatant was transferred to a clean microcentrifuge tube. The DNA concentration was determined by UV absorption at 260 nm.

Example 2

DNA SEQUENCING

The target tRNA$^{Lys}$ and ATP synthase subunit 8 DNA sequences were amplified by polymerase chain reaction (PCR) (Erlich et al., Nature 331:461–462 (1988)). Primers were designed using the published Cambridge sequences for normal human mitochondrial DNA. (Anderson et al., Nature 290:457 (1981)). Three primer pairs were designed with sequences homologous to the tRNA$^{Lys}$ and the ATP synthase subunit 6 DNA sequences (forward and reverse primers #1 H and #1 L, respectively, Table 1, SEQ ID NO:1 and SEQ ID NO:2), to the cytochrome oxidase subunit 2 and the ATP synthase subunit 8 DNA sequences (forward and reverse primers #2 H and #2 L, respectively, Table 1, SEQ ID NO:3 and SEQ ID NO:4), and to the tRNA$^{Lys}$ and the ATP synthase subunit 8 DNA sequences (forward and reverse primers #3 H and #3 L, respectively, Table 1, SEQ ID NO:5 and SEQ ID NO:6).

Primers were chemically synthesized using an ABI 394 DNA/RNA synthesizer (Applied Biosystems Division, Perkin Elmer Corp.) using betacyanoethylphosphoramidite chemistry. The primers were deprotected with ammonium hydroxide and purified using Oligonucleotide Purification Cartridges (ABI, Perkin Elmer Corp.).

TABLE 1

NIDDM: PCR PRIMERS

| SEQ ID NO: | PRIMER | STRAND | LENGTH | POSITION | SEQUENCE 5'->3' |
| --- | --- | --- | --- | --- | --- |
| 1 | Forward Primer | #1L | 23mer | 8292 | GCCCACTGTAAAGCTAACTTAGC |
| 2 | Reverse Primer | #1H | 22mer | 8631 | TAGTCGGTTGTTGATGAGATAT |
| 3 | Forward Primer | #2L | 23mer | 8059 | CGTCTTGCACTCATGAGCTGTCC |
| 4 | Reverse Primer | #2H | 25mer | 8513 | ATTTTCGTTCATTTTGGTTCT-CAGG |
| 5 | Forward Primer | #3L | 25mer | 8311 | TAGCATTAACCTTTTAAGT-TAAAGA |
| 6 | Reverse Primer | #3H | 19mer | 8516 | TCGTTCATTTTGGTTCTCA |

Amplification was performed using 0.5–1.0 μg DNA in a reaction volume of 50–100 μl, containing 10 mM Tris HCl (pH 8.3), 50 mM potassium chloride, 2 mM magnesium chloride, 200 μM each of deoxy-ATP, deoxy-CTP, deoxy- GTP and deoxy-TTP (Amplification cocktail), 200 ng each of the appropriate forward and reverse primers and 5 units of AmpliTaq polymerase (Applied Biosystems Division, Perkin Elmer Corp., Foster City, Calif.; catalogue # N801–0060).

Amplification using primer pairs #1 (SEQ ID NO: 1–2) and #2 (SEQ ID NO:3–4) was allowed to proceed for one cycle at 95° C. for 10 seconds, 25 cycles at 95° C. for 1 minute, 60° C. for 1 minute, 72° C. for 1 minute, 1 cycle at 72° C. after which the samples were cooled to 4° C. Amplification using primer pair #3 (SEQ ID NO:5–6) was allowed to proceed for one cycle at 95° C. for 10 seconds, 25 cycles at 95° C. for 1 min., 50° C. for 1 min., 72° C. for 1 min. 1 cycle at 72° C. for 4, min., after which the samples were cooled to 4° C. Thermocycling reactions were performed using the GeneAmp PCR system 9600 (Applied Biosystems Division, Perkin Elmer Corp., Foster City, Calif.). Four separate amplification reactions were performed for each DNA sample. After the 4 reactions were complete, the reaction products were pooled for each patient and subunit. The pooled product was precipitated at −80° C. by the addition of 1/10 volume of 5M sodium chloride and 2 volumes of 100% ethanol.

The PCR amplification product was pelleted by centrifugation, dried, resuspended in 40 µl of TE buffer and purified by agarose gel electrophoresis. DNA was stained with ethidium bromide and visualized under long-wavelength ultraviolet light. Bands were excised from the gel, minced and placed into a microcentrifuge tube to which 0.3 ml of 1M sodium chloride was added. The tube and contents were frozen at −80° C., thawed and incubated at 40° C. for 15–20 minutes. The agarose was sedimented by centrifugation at 14,000 ×g for 5 minutes. The supernatant containing the DNA was transferred to a new vial and the DNA was collected by ethanol precipitation.

The amplified DNA was cloned into plasmid pCRII (Invitrogen Corp., San Diego, Calif.) using the TA-cloning Kit (Invitrogen Corp., San Diego, Calif.). Ligations are performed in a reaction volume of 11 µl containing 1–5 µl of PCR amplification product, 2 µl (50 ng) of plasmid, 2 µl of 10×ligation buffer, and 1 µl of T4 DNA ligase (4 units). Ligation reactions were incubated at 10–12° C. for 15–16 hours.

Vector-ligated PCR fragments were transformed into competent *E. coli* cells of the strain XL1-Blue MRF' (Stratagene, San Diego, Calif.). Transformed cells were spread onto LB-agar plates containing ampicillin (50 mg/ml), kanamycin (50 mg/ml), isopropyl-β-D-thiogalactopyranoside (20 µg/ml), and X-Gal (100 µg/ml). The blue/white color selection provided by the cloning vector allows for easy detection of recombinant clones (i.e., white stained clones).

Plasmid DNA containing gene inserts was isolated using the Qiawell 96 Plasmid Purification Kit (Qiagen, Chatsworth, Calif.). Plasmid DNA was purified from 5 ml bacterial cultures. The isolated DNA was resuspended in 100 µl TE buffer. The DNA was quantitated by $A_{260}$ absorbance of a 1:50 dilution.

Sequencing reactions using double stranded plasmid DNA were performed using the Prism™ Ready Reaction DyeDeoxy™ Terminator Cycle Of Sequencing Kit (Applied Biosystems Division, Perkin Elmer Corp., Foster City, Calif.). The DNA sequences were detected by fluorescence using the ABI 373A Automated DNA Sequencer (Applied Biosystems Division, Perkin Elmer Corp., Foster City, Calif.). Oligonucleotide primers were synthesized on the ABI 394 DNA/RNA Synthesizer using standard beta-cyanoethylphosphoramidite chemistry. The following primer, sequences were synthesized: M13(−20) forward primer (5'-GTAAAACGACGGCCAG-3', SEQ ID NO:7) and M13 reverse primer (5'-CAGGAAACAGCTATGAC-3', SEQ ID NO:8).

Sequence data were analyzed by comparison with the published Cambridge sequences. (Anderson et al., *Nature* 290:457 (1981)). Mutations for each individual were compiled as summarized in Table 2.

Sequencing reactions were performed according to the manufacturer's instructions. Electrophoresis and sequence analysis are performed using the ABI 373A Data Collection and Analysis Software and the Sequence Navigator Software (Applied Biosystems Division, Perkin Elmer Corp., Foster City, Calif.). Sequencing gels were prepared according to the manufacturer's specifications. An average of ten different clones from each individual was sequenced. The resulting ATP synthase 8 and tRNA$^{Lys}$ sequences were aligned and compared with the published sequence. Differences in the derived sequence from the published sequence are noted and confirmed by sequence of the complementary DNA strand.

The open reading frame of the sequence for ATP Synthase Subunit 8 includes nucleotide positions 8366 to 8572 (Anderson et al., 1981 *Nature* 290:457). The open reading frame of the sequence for ATP synthase subunit 6 ranges from nucleotide position 8527 through 9204 including overlap of coding sequence at its 5'-end with ATP synthase subunit 8 (Anderson et al.). The sequence for the tRNA$^{Lys}$, which includes nucleotide positions 8295 to 8364, is located directly upstream of the ATP synthase sequence (Anderson et al.).

Sequence analysis of amplification products corresponding to the tRNA$^{Lys}$ and ATP synthase 8/6 sequences revealed quantitative differences in the mutational burdens at specific nucleotide positions in these sequences between patients with non-insulin dependent diabetes and controls.

Table 2 shows sequence data using primer pair #1 (SEQ ID NO:1–2) and #2 (SEQ ID NO:3–4) (Table 1) for prior amplification for each of the 15 subjects. Mutational burden at each specific nucleotide position is indicated as percentage of mutated clones per total quantity of clones sequenced.

Eight base changes were found in the tRNA$^{Lys}$ sequence (Table 2). The mutational burden at each of these nucleotide positions was elevated in most NIDDM patients. Two of the six controls also showed modest mutational burdens at several of the nucleotide positions.

Twelve nucleotide changes that would lead to amino acid changes if translated (missense mutations) were noted in the ATP synthase 8/6 sequence. An additional 26 nucleotide changes were seen in the ATP synthase 8/6 sequence (Table 2). These additional mutations do not lead to amino acid changes and thus are considered silent mutations. The level of mutational burden at each of these nucleotide positions was elevated in most NIDDM patients. Again, two of the six controls also showed modest mutational burdens at some nucleotide positions.

In general, the mutational burdens at each of these nucleotide sites in these two sequences was increased above the control levels in most patients with NIDDM. For example, the mutational burden at nucleotide position 8401 varies from 16 to 47% in NIDDM patients and from 0 to 20% in controls. The two controls exhibiting mutational burden above 15% may be presymptomatic individuals who are at risk for developing NIDDM. Levels of mutational burden above 16% at these specific nucleotide positions may indicate the presence of or risk of developing diabetes mellitus.

TABLE 2

Mutational Burden Analysis: tRNA$^{Lys}$ and Synthase Subunits 8/6

Part A

|  |  |  | tRNA$^{Lys}$ | | | | | | | | ATP Synthase Subunit 8 | | | | | | | | | | | | | | | | |
|---|---|---|---|---|---|---|---|---|---|---|---|---|---|---|---|---|---|---|---|---|---|---|---|---|---|---|---|
|  |  | NUCLEOTIDE # | 8305 | 8310 | 8336 | 8338 | 8345 | 8348 | 8349 | 8351 | 8371 | 8374 | 8383 | 8386 | 8392 | 8395 | 8396 | 8398 | 8401 | 8404 | 8410 | 8419 | 8422 | 8423 | 8428 | 8450 |
|  |  | AMINO ACID WT | N/A | N/A | N/A | N/A | N/A | N/A | N/A | N/A | Pro | Gln | Thr | Thr | Trp | Pro | Thr | Thr | Met | Ile | Pro | Leu | Thr | Leu | Phe | Leu |
|  |  | AMINO ACID MT | N/A | N/A | N/A | N/A | N/A | N/A | N/A | N/A | Pro | Gln | Thr | Thr | Trp | Pro | Ala | Thr | Ile | Ile | Pro | Leu | Thr | Leu | Phe | Leu |
|  |  | NUCLEOTIDE WT | C | T | T | A | C | A | C | C | C | A | T | C | G | C | A | C | A | T | C | T | A | C | C | T |
|  |  | NUCLEOTIDE MT | T | C | C | G | T | C | T | T | A | G | C | T | A | T | G | T | C | C | A | C | G | T | T | C |
| PATIENT | AG # | DIAGNOSIS | | | | | | | | | | | | | | | | | | | | | | | | |
| EO | 289 | NIDDIM | 0 | 0 | 33 | 0 | 33 | 33 | 33 | 33 | 33 | 33 | 33 | 33 | 33 | 33 | 33 | 33 | 33 | 33 | 33 | 33 | 33 | 33 | 33 | 33 |
| EP | 293 | NIDDIM | 0 | 0 | 20 | 0 | 20 | 20 | 20 | 20 | 20 | 20 | 20 | 20 | 20 | 20 | 20 | 20 | 20 | 20 | 20 | 20 | 20 | 20 | 20 | 20 |
| FA | 306 | NIDDIM | 0 | 0 | 33 | 0 | 33 | 33 | 33 | 33 | 33 | 33 | 33 | 33 | 33 | 33 | 33 | 33 | 33 | 33 | 33 | 33 | 33 | 33 | 33 | 33 |
| EL | 283 | NIDDIM | 8 | 8 | 40 | 7 | 47 | 47 | 47 | 40 | 47 | 47 | 47 | 47 | 47 | 40 | 40 | 40 | 47 | 40 | 47 | 47 | 40 | 40 | 47 | 40 |
| ER | 300 | NIDDIM | 9 | 9 | 20 | 0 | 20 | 20 | 20 | 20 | 20 | 20 | 20 | 20 | 20 | 20 | 20 | 20 | 20 | 20 | 20 | 20 | 20 | 20 | 20 | 20 |
| 469 | 469 | NIDDIM | 12 | 12 | 17 | 4 | 21 | 21 | 21 | 17 | 21 | 21 | 21 | 21 | 21 | 17 | 17 | 17 | 21 | 17 | 21 | 21 | 17 | 17 | 21 | 17 |
| 578 | 578 | NIDDIM | 15 | 15 | 14 | 2 | 16 | 16 | 16 | 14 | 16 | 16 | 16 | 16 | 16 | 14 | 14 | 14 | 16 | 14 | 16 | 16 | 14 | 14 | 16 | 14 |
| 733 | 733 | NIDDIM | 25 | 25 | 4 | 16 | 20 | 20 | 20 | 4 | 20 | 20 | 20 | 20 | 20 | 4 | 4 | 4 | 20 | 4 | 20 | 20 | 4 | 4 | 20 | 4 |
| 909 | 909 | NIDDIM | 8 | 8 | 6 | 17 | 23 | 23 | 23 | 6 | 23 | 23 | 23 | 23 | 23 | 6 | 6 | 6 | 23 | 4 | 23 | 23 | 6 | 6 | 23 | 6 |
| KJ | 294 | CONTROL | 0 | 0 | 10 | 0 | 10 | 10 | 10 | 10 | 10 | 10 | 10 | 10 | 10 | 10 | 10 | 10 | 10 | 10 | 10 | 10 | 10 | 10 | 10 | 10 |
| PS | 314 | CONTROL | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GM | 50 | CONTROL | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| FB331 | 331 | AD | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GA | 27 | CONTROL | 18 | 18 | 2 | 18 | 20 | 20 | 20 | 2 | 20 | 20 | 20 | 20 | 20 | 2 | 2 | 2 | 20 | 2 | 20 | 20 | 2 | 2 | 20 | 20 |
| SH | 25 | CONTROL | 10 | 10 | 8 | 10 | 18 | 18 | 18 | 8 | 18 | 18 | 18 | 18 | 18 | 8 | 8 | 8 | 18 | 8 | 18 | 18 | 8 | 8 | 18 | 18 |

Part B

|  |  |  | ATP Synthase 8/6 | | | | | | | | | | | | | | | | | | | |
|---|---|---|---|---|---|---|---|---|---|---|---|---|---|---|---|---|---|---|---|---|---|---|
|  |  | NUCLEOTIDE # | 8459 | 8463 | 8467 | 8470 | 8473 | 8474 | 8485 | 8486 | 8487 | 8488 | 8491 | 8503 | 8506 | 8508 | 8509 | 8512 | 8539 | 8541 | 8557 | 8562 | 8566 | 8568 |
|  |  | AMINO ACID WT | Asn | Tyr | His | Leu | Pro | Pro | Lys | Pro | Pro | Pro | Met | Asn | Tyr | Asn | Asn | Lys | Ile | Cys | Leu | Pro | Gln | Ser |
|  |  | AMINO ACID MT | Asn | Cys | His | Leu | Pro | Thr | Lys | Ser | Leu | Pro | Ile | Asn | Tyr | Ser | Asn | Lys | Ile | Tyr | Leu | Leu | Gln | Tyr |
|  |  | NUCLEOTIDE WT | A | A | C | A | T | C | G | C | C | C | A | T | T | A | C | A | C | G | G | C | A | C |
|  |  | NUCLEOTIDE MT | C | G | T | G | C | A | A | T | T | T | T | C | C | G | T | G | T | A | A | T | G | A |
| PATIENT | AG # | DIAGNOSIS | | | | | | | | | | | | | | | | | | | | | | |
| EO | 289 | NIDDIM | 33 | 33 | 33 | 33 | 33 | 33 | 33 | 33 | 33 | 33 | 33 | 33 | 33 | 33 | 33 | 33 | 33 | 33 | 33 | 33 | 33 | 33 |
| EP | 293 | NIDDIM | 20 | 20 | 20 | 20 | 20 | 20 | 20 | 20 | 20 | 20 | 20 | 20 | 20 | 20 | 20 | 20 | 20 | 20 | 20 | 20 | 20 | 20 |
| FA | 306 | NIDDIM | 33 | 33 | 33 | 33 | 33 | 33 | 33 | 33 | 33 | 33 | 33 | 33 | 33 | 33 | 33 | 33 | 33 | 33 | 33 | 33 | 33 | 33 |
| EL | 283 | NIDDIM | 40 | 40 | 47 | 40 | 47 | 40 | 47 | 40 | 40 | 40 | 47 | 47 | 47 | 40 | 47 | 40 | 40 | 47 | 40 | 47 | 47 | 40 |
| ER | 300 | NIDDIM | 20 | 20 | 20 | 20 | 20 | 20 | 20 | 20 | 20 | 20 | 20 | 20 | 20 | 20 | 20 | 20 | 20 | 20 | 20 | 20 | 20 | 20 |
| 469 | 469 | NIDDIM | 17 | 17 | 21 | 17 | 21 | 17 | 21 | 17 | 17 | 17 | 21 | 21 | 21 | 17 | 21 | 17 | 17 | 21 | 17 | 21 | 21 | 17 |
| 578 | 578 | NIDDIM | 14 | 14 | 16 | 14 | 16 | 14 | 16 | 14 | 14 | 14 | 16 | 16 | 16 | 14 | 16 | 14 | 14 | 16 | 14 | 16 | 16 | 14 |
| 733 | 733 | NIDDIM | 4 | 4 | 20 | 4 | 20 | 4 | 20 | 4 | 4 | 4 | 20 | 20 | 20 | 4 | 20 | 4 | 4 | 20 | 4 | 20 | 20 | 4 |
| 909 | 909 | NIDDIM | 6 | 6 | 23 | 6 | 23 | 6 | 23 | 6 | 6 | 6 | 23 | 23 | 23 | 6 | 23 | 6 | 6 | 23 | 6 | 23 | 23 | 6 |
| KJ | 294 | CONTROL | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| PS | 314 | CONTROL | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GM | 50 | CONTROL | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| FB331 | 331 | AD | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GA | 27 | CONTROL | 2 | 2 | 20 | 2 | 20 | 2 | 20 | 2 | 2 | 2 | 20 | 20 | 20 | 2 | 20 | 2 | 2 | 20 | 2 | 20 | 20 | 2 |
| SH | 25 | CONTROL | 8 | 8 | 18 | 8 | 18 | 8 | 18 | 8 | 8 | 8 | 18 | 18 | 18 | 8 | 18 | 8 | 8 | 18 | 8 | 18 | 18 | 8 |

Example 3

NIDDM PATIENTS EXHIBIT INCREASED MUTATIONAL BURDEN IN ATP SYNTHASE 8/6 SEQUENCES

Cellular DNA from NIDDM and non-diabetic (control) patients was compared to quantify the percentage of mutant DNA molecules. Venous blood samples were collected from 24 NIDDM patients (age=49.8±4.6; body mass index, BMI=33.3 kg/m² ±0.83; 67% male, 33% female) and 15 age and weight-matched controls (age=47.3±2.1; BMI=31.6±1.0; 73% male, 27% female). The ATP synthase 8 sequence was determined as described above. Fifty clones were analyzed for each patient sample.

The percentage of mutant DNA molecules (FIG. 1) was almost twice as great (p<0.001) in the NIDDM subjects compared to the age- and weight-matched non-diabetic controls.

Example 4

SYNTHESIS OF ANTISENSE OLIGONUCLEOTIDES

Standard manufacturer protocols for solid phase phosphoramidite-based DNA or RNA synthesis using an ABI DNA synthesizer are employed to prepare antisense oligomers. Phosphoroamidite reagent monomers (T, C, A, G, and U) are used as received from the supplier. Applied Biosystems Division/Perkin Elmer, Foster City, Calif. For routine oligomer synthesis, 1 μmole scale synthesis reactions are carried out utilizing THF/$I_2$/lutidine for oxidation of the phosphoramidite and Beaucage reagent for preparation of the phosphorothioate oligomers. Cleavage from the solid support and deprotection are carried out using ammonium hydroxide under standard conditions. Purification is carried out via reverse phase HPLC and quantification and identification is performed by UV absorption measurements at 260 nm, and mass spectrometry.

Example 5

INHIBITION OF MUTANT MITOCHONDRIA IN CELL CULTURE

Antisense phosphorothiodate oligomer complementary to the ATP synthase and tRNA$^{Lys}$ sequences and thus non-complementary to wild-type ATP synthase or tRNA$^{Lys}$ sequences are added to fresh medium containing Lipofectin® (Gibco BRL,Gaithersburg, Md.) at a concentration of 10 pg/ml to make final concentrations of 0.1, 0.33, 1, 3.3, and 10 μM. These are incubated for 15 minutes then applied to the cell culture. The culture is allowed to incubate for 24 hours and the cells are harvested and the nucleic acids (DNA and/or RNA) isolated. These nucleic acids are amplified, cloned and sequenced to generate sequence data for mutational burden analysis using the sequence of Anderson et al. (1981) as described above in Example 2.

Example 6

INHIBITION OF MUTANT MITOCHONDRIA IN VIVO

Mice are divided into six groups of 10 animals per group. The animals are housed and fed as per standard protocols. Antisense phosphorothioate oligonucleotide complementary to mutant ATP synthase gene RNA, prepared as described above, is administered intramuscularly (I.M.) to groups 1 to 4, in the following amount: 0.1, 0.33, 1.0 and 3.3 umol each in 5 μL. To group 5 is administered I.M. 1.0 nmol in 5 μL of phosphorothioate oligonucleotide non-complementary to mutant ATP synthase gene RNA and non-complementary to wild-type ATP synthase gene RNA. To group 6 is administered I.M. vehicle only. Dosing is performed once a day for ten days. The animals are sacrificed and samples of muscle and pancreas collected. This tissue is treated as previously described and the nucleic acid DNA isolated and quantitatively analyzed as in previous examples. Results show a decrease in mutant ATP synthase nucleic acid to a level of less than 1% of total ATP synthase for the antisense treated group and no decrease for the control group.

Example 7

GENERATION OF CYBRID CELLS

The human neuroblastoma cell line SH-SY5Y was depleted of mitochondrial DNA by prolonged culture in the presence of ethidium bromide to yield ρ⁰ cells, as previously described. (Miller et al., *J. Neurochem.* 67:1897 (1996)) To produce mitochondrial cybrid cell lines from the ρ⁰ cells, blood-derived platelets were used as sources of donor mitochondria. Platelet-enriched buffy coat fractions were isolated from fresh venous blood donated by normal and diabetic patients, and were then fused with the ρ⁰-SH-SY5Y cells. In this way, mitochondrial DNA-encoded subunits of the electron transport complexes and ATP synthase in each cybrid cell line are transcribed entirely from the mitochondrial DNA donated by a patient's mitochondria. Using this technique, cell lines that express mitochondrial populations from individual normal donors or diabetic patients were constructed. Several analyses were performed to assess the phenotype (function) and genotype (DNA sequences) of the mitochondria in these cell lines.

Example 8

REACTIVE OXYGEN SPECIES PRODUCTION IN CYBRID CELLS DERIVED FROM DIABETIC PATIENT MITOCHONDRIA

Production of reactive oxygen species (ROS) was measured in cybrid cell lines as a general indicator of mitochondrial function. Cybrid cell lines produced using mitochondria from normal (wild-type control) or NIDDM patients were grown in 96-well plates and then incubated in the presence of the fluorescent dye 2', 7'-dichlorodihydrofluorescein diacetate (DCFC, 30 μM; Molecular Probes, Eugene, Oreg.) in Hanks balanced salt solution (HBSS) for 2 hr at 37° C. (Miller et al., *J Neurochem.* 67:1897 (1996)) The cells were washed twice with HBSS, and the fluorescence was read 30 min later at an excitation wavelength of 485 nm, emission wavelength 530 nm in a Cytofluor fluorescence plate reader. ROS production was proportional to the increase in DCFC fluorescence in the cells.

Figure 2:
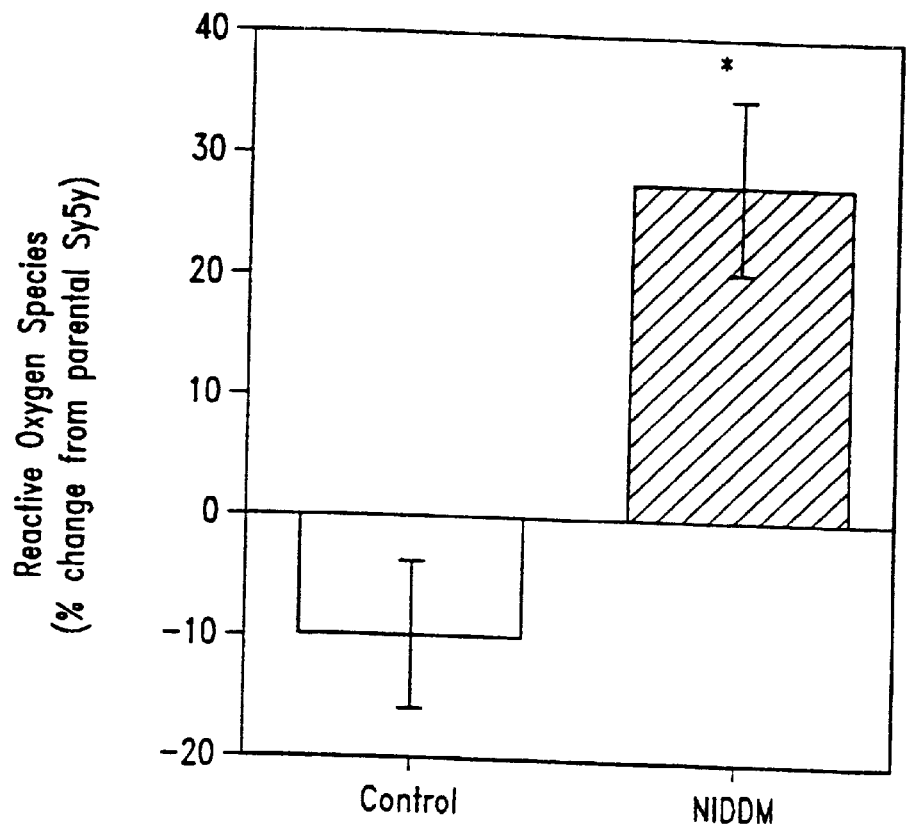
FIG. 2 depicts production of reactive oxygen species (ROS) by NIDDM and control cybrid cells.

A striking increase in the generation of ROS was observed in the NIDDM cybrids when compared to normal control cybrid cells (FIG. 2). Since the control and NIDDM cybrids differ only in their mitochondria, this finding suggested that NIDDM cybrids contain causative mitochondrial defects.

Example 9

MITOCHONDRIAL ENZYME ACTIVITY IN CYBRID CELLS DERIVED FROM DIABETIC PATIENT MITOCHONDRIA

Catalytic activities of three distinct mitochondrial enzyme complexes were measured in cybrid cell lines produced using NIDDM or normal (wild-type control) patient-derived mitochondria At least some of the constituent enzyme subunits in each of these mitochondrial protein complexes are encoded by mitochondrial genes. Defective catalytic activity in any of these complexes suggests the specific site of diabetes-associated defective mitochondrial function.

Cybrid cell lines grown in culture were harvested by trypsinization and lysed by the addition of digitonin (0.005% w/v) and EDTA (5 mM) in HBSS for 20 sec at 23° C. Fifty volumes HBSS were then added and the suspension centrifuged at 14,000 ×g for 10 min at 4° C. The pellet was resuspended in HBSS containing EDTA (5 mM), leupeptin (1 μM), pepstatin (1 μM) and phenylmethylsulfonyl fluoride (100 μM) at a final protein concentration of 3–6 mg/ml. A 200 μl aliquot of the resultant submitochondrial particulate fraction ("sample") was sonicated for 6 min at 50% duty cycle (w/v) at 50% power in an ice-packed cup horn sonicator (Branson Sonifier 450, Danbury, Conn.) immediately prior to assay.

Complex I (NADH:ubiquinone oxidoreductase) activity was measured by sequentially adding NADH (100 µM final concentration), 100 µg/ml sample protein, and coenzyme $Q_1$ (Eisai Pharmaceuticals, Tokyo, Japan; 42 µM final concentration) to prewarmed 30° C. assay buffer (25 mM potassium phosphate, ph8.0, 0.25 mM EDTA, 1.5 mM potassium cyanide). The absorbance change at 340 nm was monitored spectrophotometrically for 2 min, after which 2.5 µM rotenone was added for an additional 2 min.

Complex IV (cytochrome c oxidase) activity was measured as described (Parker et al., *Neurology* 40:1302–1303 (1990)) except that sample submitochondrial particulate fractions were prepared as described above and assay reaction volumes were reduced. Assay reactions were initiated by addition of reduced cytochrome c to spectrophotometer cuvettes containing sample aliquots, and the change in absorbance at 550 nm was measured continuously for 90 sec. The fully oxidized absorbance value was determined by the addition of a few grains of fenricyanide to the cuvette. Rates were obtained at various sample concentrations to validate that the assay was in the linear range. Non-enzymatic background activity was determined by preincubation of sample with 1 mM potassium cyanide prior to determination of the rate constant.

Complex V (ATP synthase) activity was determined by incubating samples containing 1 mg protein with 1 mM ATP, 0.3 mM NADH, 10 U/ml LDH, 1 mM phosphoenolpyruvate, and 2.5 U/ml pyruvate kinase in 50 mM Tris-HCl buffer, pH 8.0 at 30° C. in a total volume of 1 ml. The change in absorbance at 340 nm was monitored spectrophotometrically for 10 min, and all activities were normalized to total cellular protein.

The activities of complex I and complex IV were not different in submitochondrial particles prepared from normal control and NIDDM cybrid cell lines (Table 3), indicating that mutations of mitochondrial genes encoding complex I and complex IV subunits are not likely responsible for the mitochondrial dysfunction manifested as elevated ROS production in NIDDM cybrids.

In contrast, complex V (ATP synthase) activity was decreased 35% in NIDDM cybrids when compared to control cybrids.

These results suggest that decreased ATP synthase activity is responsible for the observed mitochondrial dysfunction, namely increased ROS production. To test the alternative hypothesis, i.e., that increased ROS generation could somehow cause decreased ATP synthase activity, complex V activity was measured in cybrids generated using mitochondria from Alzheimer's Disease (AD) patients. Like the NIDDM cybrids, AD cybrids produced increased ROS compared to normal (wild-type) control cybrids. However, ATP synthase activity levels in AD cybrids were comparable to those in normal control cybrids. (data not shown) Thus decreased cybrid cell ATP synthase activity is not a consequence of excessive ROS production, but instead appears to be causally related to ROS generation (FIG. 2).

TABLE 3

Electron Transport Chain Activities in Control and NIDDM Cybrid Cell Lines

| Cybrid | Complex I (µM/min/mg) | Complex IV ($min^{-1}$ $mg^{-1}$) | Complex V (ATP Synthase) (nmol/min/mg) |
|---|---|---|---|
| Control | 27.5 ± 1.2 | 2.05 ± 0.06 | 17.1 ± 1.2 |
| NIDDM | 26.6 ± 0.84 | 1.92 ± 0.29 | 11.2 ± 0.88 |

Example 10

NIDDM CYBRID CELLS CONTAIN DEFECTIVE MITOCHONDRIA

Defective mitochondrial function, and specifically defective ATP synthase 8 activity, were observed in cybrid cells generated by fusing $\rho^0$ cells with platelets derived from NIDDM patients, as described above. To determine the ATP synthase 8 mutational burden, DNA from a NIDDM cybrid cell line was prepared and analyzed by slot blot hybridization.

Total cellular DNA was extracted from a NIDDM cybrid cell line and from $\rho^0$ cells. One microgram of DNA was loaded into each slot of a slot blot apparatus. Duplicate slot blots were probed with [$^{32}$P]-labeled oligonucleotide probes specific for wild-type or mutant ATP synthase 8 gene sequences under hybridization and washing conditions that produced ≧97% specificity for each probe. The wild-type probe was a fragment corresponding to base pairs 8831–8536 in the mitochondrial genome (Anderson et al., *Nature* 290:457 (1981)), while the mutant probe was a fragment corresponding to base pairs 8326–8526 in the mitochondrial genome, and contained the point mutations presented in Table 2.

The signal corresponding to mitochondrial DNA was undetectable in $\rho^0$ cells. The mutant ATP synthase 8/6 sequence was readily detectable in the NIDDM cybrid-derived DNA. Quantitation of the blots revealed that these diabetic cells exhibited a mutational burden of approximately 20%. This observation confirms that the increased ATP synthase 8/6 mutational burden was successfully transferred into the NIDDM cybrid cells along with the donor patients' mitochondria. This result also demonstrates mutational burden in a NIDDM patient mitochondrial sample, since both wild-type and mutant ATP synthase 8/6 sequences were detected.

From the foregoing it will be appreciated that the description of the invention and the various embodiments thereof is intended to be illustrative and not limiting. Although the invention has been described with reference to the above-provided examples, it should be understood that various modifications can be made without departing from the spirit of the invention.

What is claimed is:

1. An isolated nucleotide sequence which is at least partially complementary to a mitochondrial DNA sequence, wherein said isolated sequence contains at least one mutation in an ATP synthase subunit 8/6 gene which correlates with the presence or risk of diabetes mellitus.

2. An isolated nucleotide sequence which is at least partially complementary to a mitochondrial DNA sequence, wherein said isolated sequence contains at least one mutation in a tRNA$^{Lys}$ gene which correlates with the presence or risk of diabetes mellitus.

3. An isolated nucleotide sequence which is at least partially complementary to a mitochondrial DNA sequence, wherein said isolated sequence contains at least one mutation located between mitochondrial DNA nucleotides 8295 and 8571 which correlates with the presence or risk of diabetes mellitus.

4. The isolated nucleotide sequence of any one of claims 1–3 wherein said isolated sequence is labelled with a detectable agent.

5. An isolated nucleotide sequence which is at least partially complementary to a mitochondrial DNA sequence, said isolated sequence having a mutational burden at one or more nucleotide positions in a sequence region corresponding to a wildtype mitochondrial DNA sequence, wherein the mutational burden correlates with the presence of or risk of developing diabetes mellitus.

* * * * *

UNITED STATES PATENT AND TRADEMARK OFFICE
CERTIFICATE OF CORRECTION

PATENT NO.    : 6,291,172 B1
DATED         : September 18, 2001
INVENTOR(S)   : Robert E. Davis and Corina Herrnstadt It is certified that error appears in the above-identified patent and that said Letters Patent is hereby corrected as shown below:

<u>Title page,</u>
Item [56], References Cited, the following FOREIGN PATENT DOCUMENT should appear as follows:
-- WO93/24650   12/1993   (WO) . --.

Signed and Sealed this

Sixteenth Day of July, 2002

*Attest:*

*Attesting Officer*

JAMES E. ROGAN
*Director of the United States Patent and Trademark Office*